United States Patent [19]

Rousseau

[11] Patent Number: 4,690,643
[45] Date of Patent: Sep. 1, 1987

[54] DENTAL FASTENING DEVICE AND METHOD OF USE

[76] Inventor: Carl H. Rousseau, 1510 Barry St., Clearwater, Fla. 33516

[21] Appl. No.: 838,245

[22] Filed: Mar. 10, 1986

[51] Int. Cl.$^4$ ............................................. A61C 11/00
[52] U.S. Cl. ................................... 433/213; 433/229; 264/16
[58] Field of Search ............... 433/213, 229, 171, 167; 264/16, 17, 18, 19

[56] References Cited

U.S. PATENT DOCUMENTS

| | | | |
|---|---|---|---|
| 2,755,552 | 7/1956 | Brandau | 264/16 |
| 3,576,075 | 4/1971 | Scott | 433/213 |
| 3,882,602 | 5/1975 | Polanco | 433/213 |
| 4,059,899 | 11/1977 | Dyal | 433/171 |

*Primary Examiner*—John J. Wilson
*Attorney, Agent, or Firm*—Frijouf, Rust & Pyle

[57] ABSTRACT

A dental fastening device is disclosed for fastening a wax substructure of a subsequently fabricated dental bridge adjacent to a first and second dental die during the fabrication and shaping of the wax coping or substructure. The substructure includes a pontic portion disposed between a first and a second abutment portion. The fastening device inhibits relative movement between the pontic and abutment portions during solidification and shrinkage of the substructure. The fastening device comprises a first elongate tie down member having a first and a second end. The first end of the first tie down member is anchored to the lingual face of a cast adjacent to the first die and the second end of the first tie down member is anchored to the buccal face of the cast adjacent to the first die. The first tie down member extends from the lingual face of the cast over the occlusal surface of the first abutment portion and around the buccal face of the cast. A second tie down member includes a first and a second end, the second member fastening the second abutment portion of the wax substructure against movement relative to the second die. The second tie down member extends around the second abutment portion of the substructure such that during the hardening and inherent shrinkage of the wax substructure, the first and second tie down member cooperate together for inhibiting relative movement between the pontic portion and the adjacent abutment portions of the wax substructure so that the subsequently fabricated dental bridge will be an accurate fit.

12 Claims, 11 Drawing Figures

DENTAL FASTENING DEVICE AND METHOD OF USE

BACKGROUND OF THE INVENTION

1. Field of the Invention

This invention relates to a dental fastening device. More specifically, this invention relates to a dental fastening device for fastening a wax substructure or wax coping of a subsequently fabricated dental bridge adjacent to a first and second dental die during the fabrication and shaping of the substructure where the substructure includes a pontic portion disposed between a first and second abutment portion such that the fastening device inhibits relative movement between the pontic and abutment portions during hardening and shrinkage of the substructure.

2. Information Disclosure Statement

In the fabrication of a dental bridge several steps are involved. These steps include initially taking an impression of the patient's mandible and maxillary until the subsequent fitting of the dental bridge.

More specifically, a doctor involved in the preparation of a dental bridge will take a wax impression which includes an impression of the abutment teeth and the pontic portion that is to be bridged. The impression will then be sent to a dental laboratory for fabrication of the bridge.

In the case of a patient requiring a standard bridge extending from a first to a second abutment tooth, the pontic portion is that portion disposed between the first and second abutment teeth. This type of bridge is provided primarily as a prosthetic device in order to serve the purpose of the tooth that previously occupied the position of the pontic portion of the dental bridge.

As will be well known to those skilled in the art, several variations of the standard bridge have been fabricated in dental laboratories including cantilever bridges in which a pontic portion is bridged to an adjacent abutment tooth. Furthermore, more than two suitably prepared abutment teeth may be spanned by a plurality of pontic portions according to the particular need of the patient being treated.

Particularly with regard to the present invention, a standard bridge will be exemplified in which a first and second abutment tooth are prepared for the subsequent fitting thereto of a bridge with a pontic portion disposed between abutment portions of the bridge.

When the doctor has taken an impression of the patient's mandible and maxillary including an impression of the first and second abutment teeth and the intervening pontic portion, these impressions will be sent to a dental laboratory for fabrication of the bridge.

The dental laboratory will use the impression of the first and second abutment teeth and intervening pontic portion to provide a replica of that portion of the patient's jaw in "stone". Usually, this "stone" replica or cast is of plaster of paris or other hardenable material. When the cast replica has been formed, the first and second abutment tooth replicas and the pontic portion will be cut from the cast and the individual replicas of the teeth and pontic portion known in the art as dies are individually mounted and are correctly aligned on the cast. Such alignment is accomplished with the aid of a dental articulator in which a replica of the corresponding opposite jaw of the patient is used to insure correct alignment and positioning of the first and second abutment teeth dies and the intervening pontic portion die.

After the removal of any undesirable undercut portions on the dies, the dental technician will hand wax the first and second abutment dies and the intervening pontic die such that the pontic portion of the substructure extends between the first and second abutment portions of the substructure. One way of hand waxing is accomplished by dipping the die in a preheated wax bath such that an even coating of wax known in the art as a coping adheres to the die.

In the prior art, problems have existed at this stage of fabrication because as the wax hardens and shrinks over the surface of the abutment dies, there exists a strong tendency for the connecting portions or interproximal areas between the abutment portions and pontic portion respectively to shrink or move relative to each other. Such relative movement results in a badly fitting dental bridge. The wax substructure or coping is used in the fabrication of a subsequently formed metal bridge by the well known lost wax or investment casting process and because of the resultant metal bridge is a replica of the wax coping, any imperfections in the coping will be reproduced in the metal bridge. Therefore, the resultant metal casting will be a replica of the distorted wax substructure.

The present invention seeks to overcome the problem of relative movement between the abutment portions of the wax substructure and the pontic portion thereof by providing tie downs which extend around the abutment portions of the wax substructure to firmly fasten the abutment portions in place during hardening and shrinkage thereof.

Therefore it is a primary objective of the present invention to provide a dental fastening device which overcomes the aforementioned inadequacies of the prior art devices and to provide a method of fastening the abutment portions of a wax substructure during hardening and shrinkage of the substructure to provide a subsequently fabricated dental bridge that will be an accurate fit.

Another object of the present invention is the provision of a dental fastening device in which movement between connecting portions or interproximal areas between the abutment portions and pontic portions respectively is inhibited.

Another object of the present invention is the provision of a dental fastening device in which the elongate tie down members are of elastomeric material such that the abutment portions of the wax substructure will be urged into mating engagement with the corresponding abutment dies.

Another object of the present invention is the provision of a dental fastening device in which each of the tie down members define at least one longitudinal slit disposed in the vicinity of the occlusal surface of the abutment portion of the wax substructure such that relative rotation between the wax substructure of the abutment portion and the corresponding dental die is inhibited.

The foregoing has outlined the pertinent objects of the present invention. These objects should be construed to be merely illustrative of some of the more prominent features and applications of the invention. Many other beneficial results can be attained by applying the disclosed invention in a different manner or modifying the invention within the scope of the disclosure. Particularly with regard to the use of the invention disclosed herein, this should not be construed as limited to the provision of dental fastening devices for the subsequent fabrication of standard dental bridges but should include fastening devices for inhibiting relative movement between the abutment portions and pontic portions of a wax substructure which includes a plurality of abutment portions and a plurality of pontic portions.

SUMMARY OF THE INVENTION

The dental fastening device of the present invention is defined by the appended claims with the specific embodiment shown in the attached drawing. For the purpose of summarizing the invention, the invention relates to a dental fastening device and method for fastening a wax substructure of a subsequently fabricated dental bridge adjacent to a first and second dental die during the fabrication and shaping of the substructure. The substructure includes a pontic portion disposed between a first and second abutment portion. The fastening device inhibits relative movement between the pontic and abutment portions during hardening and shrinkage of the substructure. The fastening device comprises a first elongate tie down member having a first and a second end. The first member fastens the first abutment portion of the wax substructure against movement relative to the first die. The first end of the first tie down member is anchored to the lingual face of a cast adjacent to the first die and the second end of the first tie down member is anchored to the buccal face of the cast adjacent to the first die. The first tie down member extends from the lingual face of the cast adjacent to the first die over the occlusal surface of the first abutment portion and around to the buccal face of the cast adjacent the first die. A second tie down member includes a first and a second end. The second member fastens the second abutment portion of the wax substructure against movement relative to the second die. The first end of the second tie down member is anchored to the lingual face of the cast adjacent to the second die. The second end of the second tie down member is anchored to the buccal face of the cast adjacent to the second die and the second tie down member extends from the lingual face of the cast adjacent to the second die over the occlusal surface of the second abutment portion and around to the buccal face of the cast adjacent to the second die such that during hardening and the inherent shrinkage of the wax substructure, the first and the second tie down members cooperate together for inhibiting relative movement between the pontic portion and the adjacent abutment portions of the wax substructure so that the subsequently fabricated dental bridge will be an accurate fit.

More particularly, the first and second tie down members are of elastomeric material such as rubber having a 50% elastic capacity. Each of the tie down members includes a first and a second band each having a first and a second end such that the first ends of the first and second bands are secured to each other and the second ends of the first and second bands are joined to each other such that the first and second bands are disposed adjacent to the occlusal surface of the adjacent die and spaced relative to each other such that the first and second bands respectively cooperate together to urge the corresponding abutment portion of the substructure into mating engagement with the die.

The first and second tie down members alternatively include a plurality of longitudinal slits defined by each tie down member such that the slits inhibit rotational movement of the respective abutment portions relative to the adjacent die.

The first and second ends of the tie down members are each anchored to the respective faces of the base of the first and second dies by sticky wax such as vinyl acrylate.

The foregoing has outlined rather broadly the more pertinent and important features of the present invention in order that the detailed description that follows may be better understood so that the present contribution to the art may be fully appreciated. Additionally, features of the invention will be described hereinafter which form the subject of the claims of the invention. It should be appreciated by those skilled in the art that the conception and the specific embodiment disclosed may be readily utilized as a basis for modifying or designing other devices for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
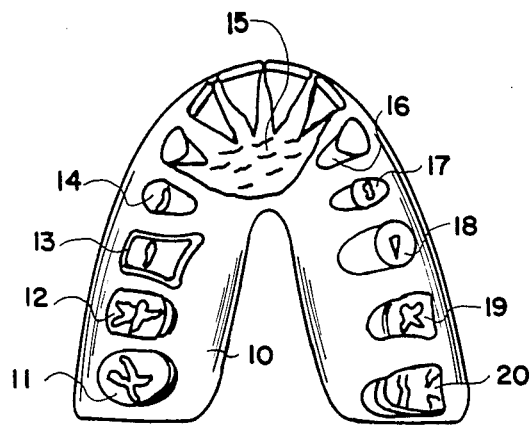
FIG. 1 is a top plan view of a cast replica of a patient's palate and alveolar arch.

FIG. 1 is a top plan view of a cast replica of the palate and alveolar arch of a patient. The cast replica includes a cast 10 and a plurality of dies 11, 12, 13, 14, 15, 16, 17, 18, 19 and 20. Dies 16–18 are prepared for the application thereto of a wax substructure to be described hereinafter. The cast 10 and dies 11–20 are fabricated at a dental laboratory by using an impression (not shown) provided by the doctor who has taken an impression of the upper palate and lower jaw of the patient. In order to carry out work on the cast 10 the individual replicas of the teeth are cut from the cast 10 and are individually, with the exception of 15, mounted on the cast 10 such that the dies 11-20 may individually be removed from the cast 10.

Figure 2:
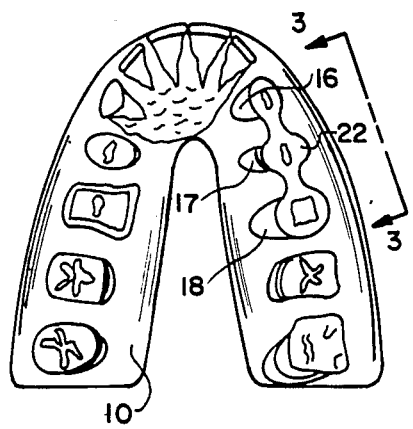
FIG. 2 is a similar view to that shown in FIG. 1 but shows a wax substructure or coping applied to the abutment dies and an intervening pontic die.

FIG. 2 shows a wax substructure 22 having been applied to the prepared portion of dies 16, 17 and 18 respectively. Prior to the application of the wax substructure or coping 22, the dies 16-18 are prepared by the removal therefrom of any undercut portions or the like. The application of wax to the two abutment dies 16 and 18 and the intervening pontic portion 17 is accomplished by the dental technician by simultaneously dipping the abutment dies 16 and 18 and intervening pontic die 17 into a wax bath as is well known to those skilled in the art. Alternatively, the application of wax or the like is accomplished by an incremental build-up technique.

Figure 3:
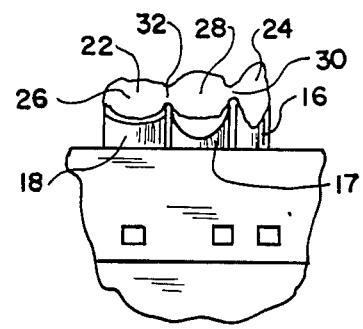
FIG. 3 is a view taken on the line 3—3 of FIG. 2.

In the prior art it has been customary for the dental technician to allow the wax to solidify around the abutment dies 16 and 18 and the pontic die 17. However, in the prior art a problem has existed in that as the wax hardens there is a tendency for the wax to shrink thereby resulting in a slight distortion of the wax substructure or coping relative to the abutment dies 16 and 18 and pontic portion 17. As will be seen particularly with reference to FIG. 3, the wax substructure 22 includes a first abutment portion 24, a second abutment portion 26 and an intervening pontic portion 28. The pontic portion 28 of the wax substructure 22 is joined to the first abutment portion 24 by a first neck portion 30. The pontic portion 28 is joined to the second abutment portion 26 by means of a second neck portion 32. It will be apparent to those skilled in the art that as the substructure 22 shrinks or if there is relative rotational or twisting of the substructure 22 relative to the dies 16-18, the resultant metal bridge substructure (not shown) will not be an accurate fit when applied to the actual abutment teeth and intervening pontic portion of the patient's mouth.

Figure 4:
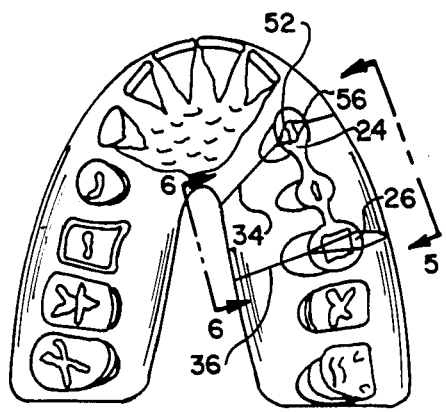
FIG. 4 is a similar view to that shown in FIG. 2 but includes a first and second tie down extending around the first and second abutment portions respectively of the wax substructure.

FIG. 4 shows the application to the first and second abutment portions 24 and 26 respectively of a first and a second elongate tie down member 34 and 36 respectively. Each of the tie downs 34 and 36 include a first end 38 and 40 as shown particularly with reference to FIG. 5. Similarly, the tie downs 34 and 36 each include a second end 42 and 44 respectively as shown in FIG. 6. The first tie down 34 extends from the buccal face 46 of the cast 10 adjacent to the first abutment die 16 around the first abutment portion 24 of the substructure 22 so that the second end 42 of the first tie down 34 which is anchored to the lingual face 48 of the cast 10 adjacent to the first die 16. The second tie down member 36 includes a first and second end 40 and 44 respectively and the first end 40 as shown in FIG. 5 is anchored to the cast 10 adjacent to the buccal face 46 of the second die 18 around the occlusal surface 50 of the second abutment portion 26 and around to the lingual face 48 of the cast 10 where it is anchored at 44 adjacent to the second die 18.

Figure 5:
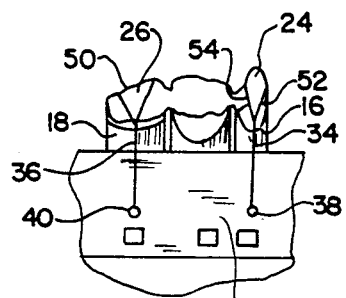
FIG. 5 is an enlarged view taken on the line 5—5 of FIG. 4.
Figure 6:
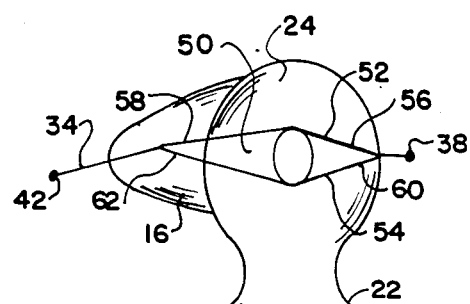
FIG. 6 is an enlarged view taken on the line 6—6 of FIG. 4.
Figure 6:
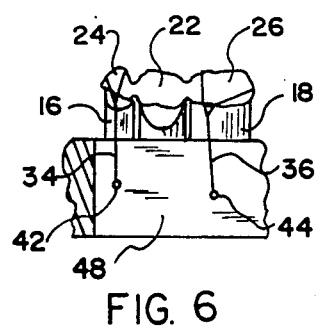
Figure 5A:
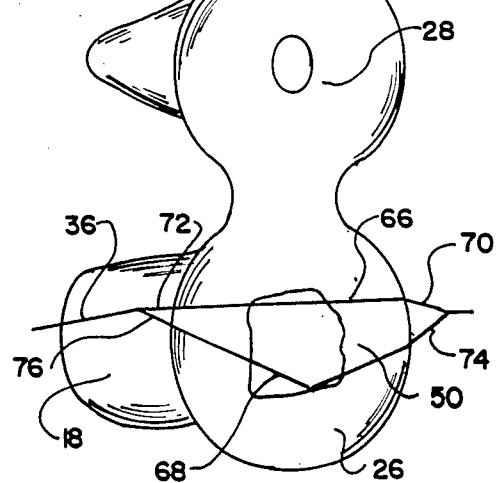
FIG. 5A is an enlarged top plan view of the coping shown in FIG. 4 showing the relative disposition of the bands relative to the coping.

As shown particular with reference to FIGS. 5, 5A and 6, the first tie down 34 includes a first and a second band 52 and 54 respectively. The first band 52 includes a first and a second end 56 and 58 respectively and the second band 54 includes a first and and a second end 60 and 62 respectively such that the first ends 56 and 60 of the bands 52 and 54 are joined together and the second ends 58 and 62 of the first and second bands 52 and 54 are joined together so that the bands are spaced relative to each other and are disposed adjacent to the occlusal surface 50 of the first portion 24 of the substructure 22.

The second tie down member generally designated 36 also includes a first and a second band 66 and 68 respectively. The first band 66 includes a first and second end 70 and 72 respectively and the second band 68 includes a first and a second end 74 and 76 respectively such that the first ends 70 and 74 of the bands 66 and 68 are joined together and the second ends 72 and 76 of the bands 66 and 68 are joined together and are disposed adjacent to the occlusal surface 50 of the second abutment portion 26 of the substructure 22 in order to urge the first and second abutment portions 24 and 26 respectively into mating engagement with the adjacent surfaces of the first and second abutment dies 16 and 18 respectively.

Preferably the first and second tie downs 34 and 36 are of elastomeric material such as rubber and have a 50% elastic capacity.

Figure 7:
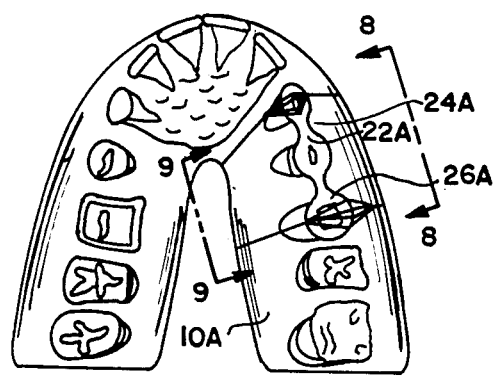
FIG. 7 is a similar view to that shown in FIG. 4 but shows the tie downs defining respectively a first and a second plurality of slits.
Figure 8:
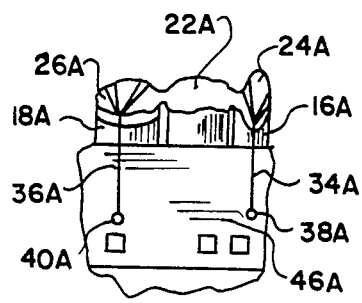
FIG. 8 is a view taken on the line 8—8 of FIG. 7.
Figure 9:
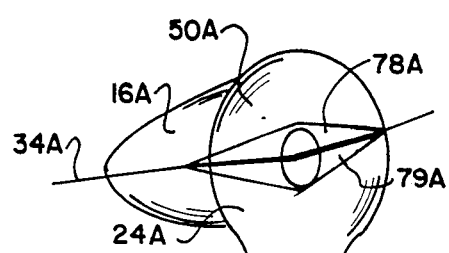
FIG. 9 is a view taken on the line 9—9 of FIG. 7.
Figure 9:
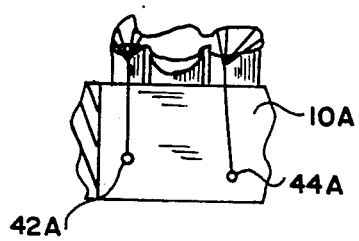
Figure 8A:
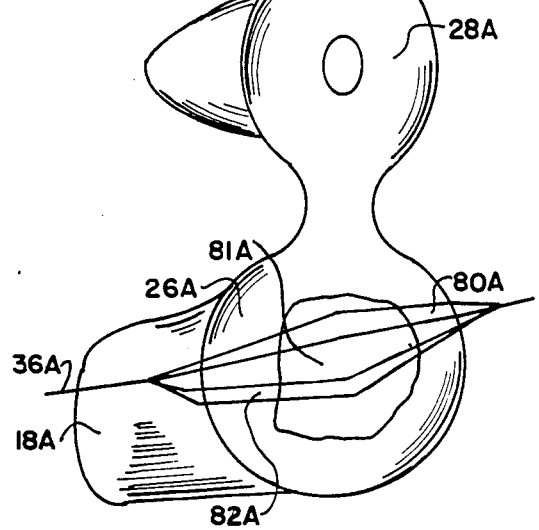
FIG. 8A is an enlarged top plan of the coping shown in FIG. 7 showing the relative disposition of the bands and intervening slits.

In a further embodiment of the present invention as shown with reference to FIGS. 7-9, similar reference characters for portion corresponding to the first embodiment are used. However, the suffix A has been added thereto. The first and second tie downs 34A and 36A respectively define a plurality of slits 78A, 79A, 80A, 81A and 82A shown in FIG. 8A such that the occlusal surface 50A of the first and second abutment portions 24A and 26A are urged into abutting relationship with the first and second abutment dies 16A and 18A thereby inhibiting rotational movement of the abutment portions 24A and 26A relative to the respective abutment dies 16A and 18A.

In both embodiments of the present invention, the first and second ends 38A, 40A, 42A and 44A of the first and second tie down members 34A and 36A are anchored to the respective faces of the cast 10A by means of sticky wax such as vinyl acrylate.

In use of the device of the present invention, a subsequently fabricated dental bridge is produced by applying a first and a second tie down member adjacent to a first and second abutment portion of the wax substructure thereby inhibiting relative movement between the wax substructure and intervening pontic portion 28 or 28A. The method includes the steps of hand waxing the pontic and abutment dies respectively such that the first abutment portion 24 or 24A of the resultant substructure is disposed adjacent to the first die and the second abutment portion 26 or 26A is disposed adjacent to the second die and the pontic portion is disposed between the first and second abutment portions. The first and second ends of the first elongate tie down member are anchored respectively to the buccal and the lingual faces of the cast 10 aor 10A adjacent to the first die 16 or 16A respectively such that the first tie down member 34 or 34A extend around the occlusal surface 50 or 50A of the first abutment portion 24 or 24A for urging the first abutment portion into mating engagement with the first die 16 or 16A.

In the first embodiment the first and the second ends 40 and 44 respectively of the second elongate tie down member 36 are anchored at 40 and 44 respectively to the buccal and lingual faces 46 and 48 of the cast 10 adjacent to the second die 18 such that the second elongate member 36 extends around the occlusal surface 50 of the second abutment portion 26 for urging the second abutment portion 26 of the substructure 22 into mating engagement with the second die 18 so that relative movement between the pontic and abutment portions 28, 24 and 26 respectively of the substructure 22 is inhibited during hardening and shrinkage of the substructure so that the subsequently fabricated dental bridge will be an accurate fit.

When the wax substructure or coping 22 has fully hardened, the tie downs 34 and 36 are removed and the wax substructure 22 is removed and transferred to an investment casting machine (not shown) for subsequent fabrication of a metallic replica of the wax substructure 22 by the lost wax investment casting process well known to those skilled in the art.

Due to the provision of the first and second tie down members 34 and 36 respectively which urge the wax substructure into mating engagement with the dies 16-18 during hardening of the wax substructure, the resultant wax substructure will faithfully maintain the same shape in reverse as that of the abutment dies 16 and 18 and intervening pontic portion 17. Therefore, the resultant metal cast substructure (not shown) will accurately fit over the prepared surface of the actual abutment teeth and pontic portion of the patient's mouth.

In operation of the second embodiment of the invention, the same steps are carried out as those of the first embodiment, however a greater number of bands and intervening slits are provided by the tie downs of the second embodiment, thereby increasing the positive location of the coping 22A relative the dies.

The present invention provides a significant improvement over the prior art bridges that were fabricated without the provision of any biasing tie downs, this resulting in a subsequently fabricated bridge that will accurately and securely fit adjacent to the actual abutment teeth and pontic portion of the patient's mouth.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and the arrangement of parts may be resorted to without departing from the spirit and scope of the invention.

What is claimed is:

1. A dental fastening device for fastening a wax substructure of a subsequently fabricated dental bridge adjacent to a first and second dental die of a cast during the fabrication and shaping of the substructure, the substructure having a pontic portion disposed between a first and a second abutment portion, the fastening device inhibiting relative movement between the pontic and abutment portions during hardening and shrinkage of the substructure, said fastening device comprising in combination:

a first elongate tie down member having a first and a second end, said first member fastening the first abutment portion of the wax substructure against movement relative to the first die, said first end of said first tie down member being anchored to the lingual face of the cast adjacent to the first die, said second end of said first tie down member being anchored to the buccal face of the cast adjacent to the first die, said first tie down member extending from the lingual face of the cast adjacent to the first die over the occlusal surface of the first abutment portion and around to the buccal face of the cast adjacent to the first die; and a second elongate tie down member having a first and a second end, said second member fastening the second abutment portion of the wax substructure against movement relative to the second die, said first end of said second tie down member being anchored to the lingual face of the cast adjacent to the second die, said second end of said second tie down member being anchored to the buccal face of the cast adjacent to the second die, said second tie down member extending from the lingual face of the cast adjacent to the second die over the occlusal surface of the second abutment portion and around to the buccal face of the cast adjacent to the second die such that during the hardening and inherent shrinkage of the wax substructure, said first and second die down members cooperate together for inhibiting relative movement between the pontic portion and the adjacent abutment portions of the wax substructure so that the subsequently fabricated dental bridge will be an accurate fit.

2. A dental fastening device as set forth in claim 1, wherein said first and second members are elastomeric.

3. A dental fastening device as set forth in claim 2, wherein said first and second tie members each have a 50% elastic capacity.

4. A dental fastening device as set forth in claim 1, wherein said first and second tie down member are rubber.

5. A dental fastening device as set forth in claim 4, wherein said first and second tie down members each have a 50% elastic capacity.

6. A dental fastening device as set forth in claim 1, wherein said first tie down member further includes:

a first band having a first and a second end, said first band being disposed between said first and second end of said first tie down member such that said first band is disposed adjacent to the occlusal surface of the first die;

a second band having a first and a second end, said first end of said second band being secured to the first end of said first band, said second end of said second band being secured to the said second end of said first band, said second band being disposed adjacent to the occlusal surface of the first die and spaced relative to said first band such that said first and second bands cooperate together to urge the first abutment portion into mating engagement with the first die;

said second tie down member further including:

a first band having a first and a second end, said first band of said second member being disposed between said first and second end of said second tie down member such that said first band of said second tie down member is disposed adjacent to the occlusal surface of the second die;

a second band of said second tie down member, having a first and a second end, said first end of said second band of said second member being secured to said first end of said first band of said second member, said second end of said second band of said second member being secured to said second end of said first band of said second member, said second band of said second member being disposed adjacent to the occlusal surface of the second die and spaced relative to said first band of said second member such that said first and second bands of said second member cooperate together to urge the second abutment portion into mating engagement with the second die.

7. A dental fastening device as set forth in claim 1, wherein
said first tie down member defines a first plurality of longitudinal slits disposed adjacent to the occlusal surface of the first abutment portion and spaced relative to each other for inhibiting rotational movement of the first abutment portion relative to the first die;
said second tie down member defining a second plurality of longitudinal slits disposed adjacent to the occlusal surface of the second abutment portion, said second plurality of slits being spaced relative to each other for inhibiting rotational movement of the second abutment portion relative to the second die.

8. A dental fastening device as set forth in claim 1, wherein said first and second ends of said first and second tie down members respectively are anchored to the respective faces of the cast by sticky wax.

9. A dental fastening device as set forth in claim 8, wherein said sticky wax is vinyl acrylate.

10. A dental fastening device for fastening a wax substructure of a subsequently fabricated dental bridge adjacent to a first and second dental die of a cast during the fabrication and shaping of the substructure, the substructure having a pontic portion disposed between a first and a second abutment portion, the fastening device inhibiting relative movement between the pontic and abutment portions during hardening and shrinkage of the substructure, said fastening device comprising in combination:
a first elongate tie down member having a first and a second end, said first member fastening the first abutment portion of the wax substructure against movement relative to the first die, said first end of said first tie down member being anchored to the lingual face of the cast adjacent to the first die, said second end of said first tie down member being anchored to the buccal face of the cast adjacent to the first die, said first tie down member extending from the lingual face of the cast adjacent to the first die over the occlusal surface of the first abutment portion and around to the buccal face of the cast adjacent to the cast adjacent to the first die said first tie down member being elastomeric; and
a second elongate tie down member having a first and a second end, said second member fastening the second abutment portion of the wax substructure against movement relative to the second die, said first end of said second tie down member being anchored to the lingual face of the cast adjacent to the second die, said second end of said second tie down member being anchored to the buccal face of the cast adjacent to the second die, said second tie down member extending from the lingual face of the cast adjacent to the second die over the occlusal surface of the second abutment portion and around to the buccal face of the cast adjacent to the second die, said second tie down member being elastomeric such that during the hardening and inherent shrinkage of the wax substructure, said first and second tie down members cooperate together for inhibiting relative movement between the pontic portion and the adjacent abutment portions of the wax substructure so that the subsequently fabricated dental bridge will be an accurate fit.

11. A dental fastening device for fastening a wax substructure of a subsequently fabricated dental bridge adjacent to a first and second dental die during the fabrication and shaping of the substructure, the substructure having a pontic portion disposed between a first and second abutment portion, the fastening device inhibiting relative movement between the pontic and abutment portions during hardening and shrinkage of the substructure, said fastening device comprising in combination:
a first elongate tie down member having a first and a second end, said first member fastening the first abutment portion of the wax substructure against movement relative to the first die, said first end of said first tie down member being anchored to the lingual face of the cast adjacent to the first die, said second end of said first tie down member being anchored to the buccal face of the cast adjacent to the first die, said first tie down member extending from the lingual face of the cast adjacent to the first die over the occlusal surface of the first abutment portion and around to the buccal face of the cast adjacent to the first die, said first tie down member being elastomeric, said first member defining a first plurality of longitudinal slits disposed adjacent to the occlusal surface of the abutment portion and spaced relative to each other for inhibiting rotational movement of the first abutment portion relative to the first die; and
a second elongate tie down member having a first and a second end, said second member fastening the second abutment portion of the wax substructure against movement relative to the second die, said first end of said second tie down member being anchored to the lingual face of the cast adjacent to the second die, said second end of said second tie down member being anchored to the buccal face of the cast adjacent to the second die, said second tie down member extending from the lingual face of the cast adjacent to the second die over the occlusal surface of the second abutment portion and around to the buccal face of the cast adjacent to the second die, said second tie down member being elastomeric, said second member defining a second plurality of longitudinal slits disposed adjacent to the occlusal surface of the second abutment portion and spaced relative to each other for inhibiting rotational movement of the second abutment portion relative to the second die such that during the hardening and inherent shrinkage of the wax substructure said first and second tie down members cooperate together for inhibiting relative movement between the pontic portion and the adjacent abutment portions of the wax substructure so that the subsequently fabricated dental bridge will be an accurate fit.

12. A method of fastening a wax substructure of a subsequently fabricated dental bridge adjacent to a first and second dental die during the fabrication and shaping of the substructure, the substructure having a pontic portion disposed between a first and second abutment portion, the method enabling the inhibition of relative movement between the pontic and abutment portions during hardening and shrinkage of the substructure, the method including the steps of:

hand waxing the pontic and abutment dies respectively such that the first abutment portion of the resultant substructure is disposed adjacent to the first die, the second abutment portion is disposed adjacent the second die and the pontic portion is disposed between the first and second abutment portions;

anchoring the first and second ends of the first elongate tie down member to the lingual and buccal faces of the cast adjacent to the first die respectively such that the first member extends around the occlusal surface of the first abutment portion for urging the first abutment portion into mating engagement with the first die; and anchoring the first and second ends of the second elongate tie down member to the lingual and buccal faces respectively of the cast adjacent to the second die such that the second elongate member extends around the occlusal surface of the second abutment portion for urging the second abutment portion of the substructure into mating engagement with the second die so that relative movement between the pontic and abutment portions of the substructure is inhibited during hardening and shrinkage of the substructure so that the subsequently fabricated dental bridge will be an accurate fit.

* * * * *